United States Patent [19]

George et al.

[11] Patent Number: 5,030,777
[45] Date of Patent: Jul. 9, 1991

[54] SYNTHESIS OF 3,5-DICHLOROALKYLBENZENE AND RECOVERY OF 1,3-DICHLOROBENZENE

[75] Inventors: Jacob George, Newark; Kanti B. Desai, New Castle, both of Del.; Jimmy Peress, Jamaica Estates, N.Y.

[73] Assignee: Standard Chlorine of Delaware, Inc., Delaware City, Del.

[21] Appl. No.: 429,406

[22] Filed: Oct. 31, 1989

[51] Int. Cl.$^5$ ............................................. C07C 17/12
[52] U.S. Cl. ........................... 570/202.000; 570/190; 570/194; 570/199; 570/209
[58] Field of Search .............. 570/190, 194, 202, 209, 570/199

[56] References Cited

U.S. PATENT DOCUMENTS

| | | | |
|---|---|---|---|
| 2,631,172 | 3/1953 | Schmerling | 570/194 |
| 4,629,815 | 12/1986 | Soula | 570/202 |
| 4,760,209 | 7/1988 | Blank et al. | 570/202 |
| 4,822,928 | 4/1989 | Ohtsura et al. | 570/190 |

FOREIGN PATENT DOCUMENTS 0257866  3/1988  European Pat. Off. ............ 570/190

Primary Examiner—Werren B. Lone
Attorney, Agent, or Firm—Darby & Darby

[57] ABSTRACT

A process for synthesizing 3,5-dichloroalkylbenzene and recovering 1,3-dichlorobenzene from a starting mixture of 1,3- and 1,4-dichlorobenzenes. The process includes the sequential steps of selectively alkylating the 1,3-dichlorobenzene in the starting mixture; isomerizing a portion of the 2,4-dichloroalkylbenzene produced to 3,5-dichloroalkylbenzene; separating the 1,4-dichlorobenzene from the isomeric mixture of dichlorocumenes; and selectively transalkylating the dichlorocumenes to yield alkylbenzene, 3,5-dichloroalkylbenzene and 1,3-dichlorobenzene. By selectively alkylating only a portion of the 1,3-dichlorobenzene, the reaction products are obtained in good yield and substantially free of undesirable by-products.

22 Claims, 1 Drawing Sheet

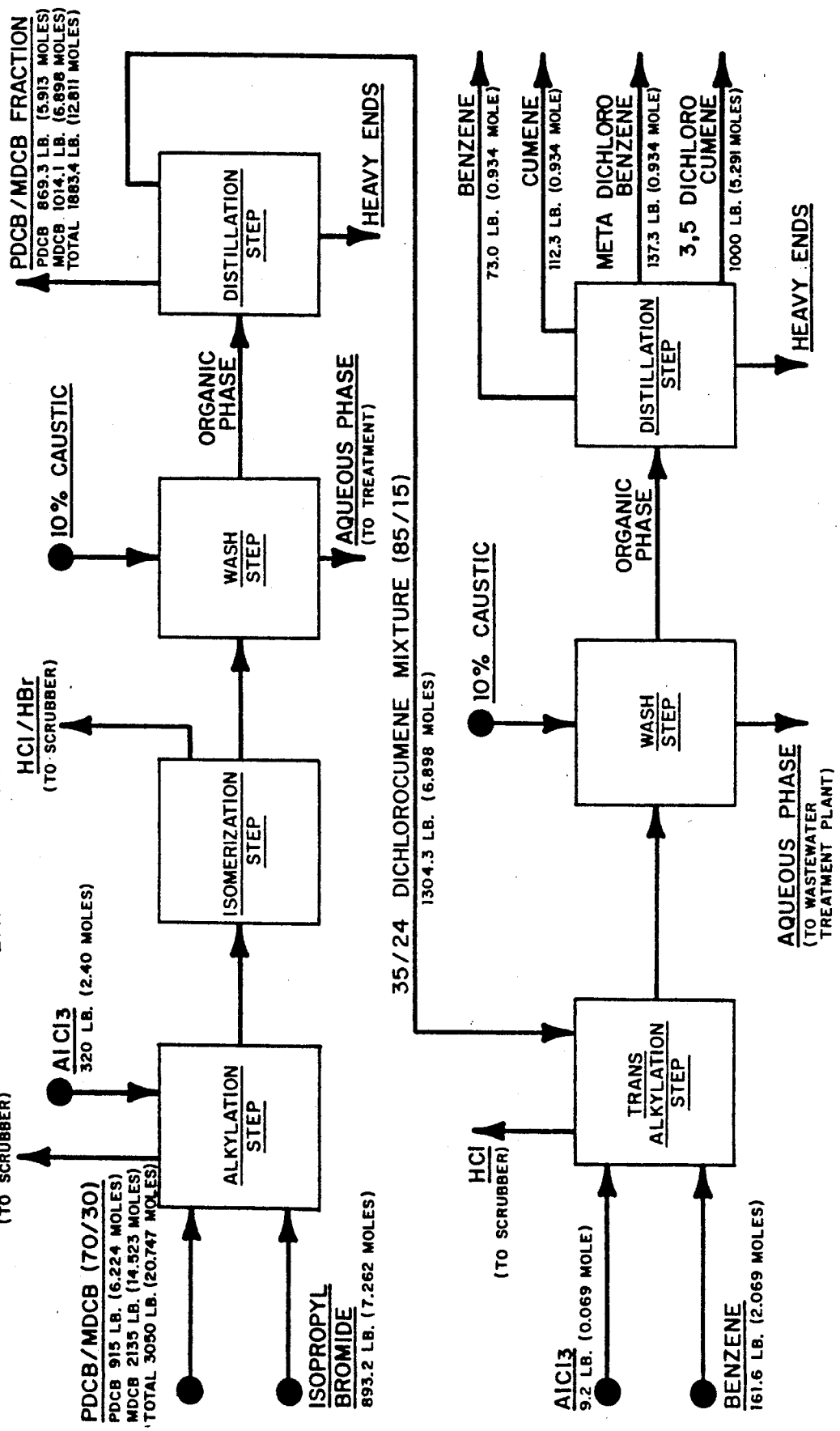

SYNTHESIS OF 3,5-DICHLOROALKYLBENZENE AND RECOVERY OF 1,3-DICHLOROBENZENE

FIELD OF THE INVENTION

This invention relates generally to processes for the synthesis of 3,5-dichloroalkylbenzene and the recovery of 1,3-dichlorobenzene and, in particular, to a process for synthesis of 3,5-dichlorocumene and the recovery of 1,3-dichlorobenzene from a mixture of 1,3- and 1,4-dichlorobenzenes.

BACKGROUND OF THE INVENTION

Chlorinated benzenes are conventionally produced by reacting benzene with chlorine. The products of the chlorination generally include monochlorobenzene, dichlorobenzenes and to a lesser extent, trichlorobenzenes, tetrachlorobenzenes, pentachlorobenzene and hexachlorobenzene. The product composition is governed by the inherent thermodynamic equilibria but may be controlled to some extent by varying reaction conditions (chlorine to benzene ratio, catalyst, temperature and residence time).

Separation of the individual products involves sequential distillations to recover unreacted benzene, monochlorobenzene and a mixture of dichlorobenzenes consisting of 1,2-dichlorobenzene, 1,3-dichlorobenzene and 1,4-dichlorobenzene. The 1,2-dichlorobenzene can be obtained in high purity by conventional distillation. The 1,4-dichlorobenzene, on the other hand, cannot be separated from 1,3-dichlorobenzene by conventional distillation because their respective boiling points are within 1° C. of each other. Most of the 1,4-dichlorobenzene can be recovered by crystallization at sub-ambient temperatures, but complete separation cannot be achieved because of the existence of a eutectic composition. Depending on the refrigeration employed, the process purge from the crystallization step may typically contain 20 to 40 percent 1,4-dichlorobenzene and 60 to 80 percent 1,3-dichlorobenzene. This mixture is not a saleable product though each of its constituents is a valuable product. For example, 1,3-dichlorobenzene is a starting raw material in the production of several new crop-protection chemicals.

U.S. Pat. No. 4,059,642 issued to Dewald et al. on Nov. 22, 1977 discloses a process for selectively alkylating a mixture of 1,3- and 1,4-dichlorobenzenes to yield a mixture of 1,4-dichlorobenzene and 2,4-dichloroalkylbenzene, which can then be separated by conventional separation techniques. As shown in the examples, isopropyl chloride is used as the alkylating agent and the dichlorobenzenes are selectively alkylated in the presence of aluminum chloride as catalyst.

U.S. Pat. No. 3,553,274 issued to Lewis et al. on Jan. 5, 1971 shows use of an $HAlBrCl_3$ catalyst to alkylate 1,3-dichlorobenzene to a mixture comprising 2,4-dichloroisopropyl benzene and 3,5-dichloroisopropyl benzene. As shown in Example 1, one mole of isopropyl bromide was used per mole of 1,3-dichlorobenzene. The yield of dichloroisopropyl benzene was only 70%.

U.S. Pat. No. 4,104,315 issued to Dewald et al. on Aug. 1, 1978, discloses a method of separating 3,5-dihaloalylbenzenes from 2,4-dihaloalkylbenzenes by selective alkylation. In an illustrative example, 2,4-dichloroisopropyl benzene was preferentially alkylated with isopropyl chloride to 2,4-dichloro-5-isopropylcumene. The unreacted 3,5-dichlorocumene was separated by simple distillation from the 2,4-dichloro-5-isopropyl cumene. As shown in the example, 90.5 percent of the 3,5-dichlorocumene present in the original mixture was removed. Unfortunately, the process leads to production of 2,4-dichloro-5-isopropylcumene which represents an undesirable by-product.

Finally, U.S. Pat. No. 4,329,524 issued to Dewald on May 11, 1982 shows a process for selectively transalkylating an isomeric mixture of 3,5- and 2,4-dichlorocumene, in the presence of excess benzene. This leads to a reaction product including cumene, 3,5-dichlorocumene and 1,3-dichlorobenzene.

None of the prior art shows a process for synthesizing 3,5-dichloroalkylbenzene and recovering 1,3-dichlorobenzene from a mixture of 1,3- and 1,4-dichlorobenzenes. The prior art also does not recognize the possibility of obtaining the above products from the alkylation of 1,3-dichlorobenzene, without production of undesirable by-products.

SUMMARY OF THE INVENTION

The subject invention is a process for synthesizing 3,5-dichloroalkylbenzene and recovering 1,3-dichlorobenzene without formation of substantial by-products using a starting mixture of 1,3- and 1,4-dichlorobenzenes. The process includes the steps of (1) selectively alkylating a mixture of 1,3 and 1,4 dichlorobenzenes to yield a mixture of 1,4-dichlorobenzene and 2,4-dichloroalkylbenzene; (2) isomerizing the 2,4-dichloroalkylbenzene in the presence of a Friedel-Crafts catalyst to yield a mixture of 1,4-dichlorobenzene, 2,4-dichloroalkylbenzene and 3,5-dichloroalkylbenzene; (3) separating the 1,4-dichlorobenzene (and unreacted 1,3-dichlorobenzene) from the mixture by distillation to leave a mixture of 2,4- and 3,5-dichloroalkylbenzenes; and (4) selectively transalkylating the 2,4-dichloroalkylbenzene in the presence of a receptor compound such as benzene to yield alkylbenzene, 3,5-dichloroalkylbenzene and 1,3-dichlorobenzene. Less than 50% of the 1,3-dichlorobenzene in the starting mixture is selectively alkylated in order to minimize unwanted by-product formation, specifically formation of di-alkyl compounds.

It is an object of the invention is to provide a process for synthesizing 3,5-dichloroalkylbenzene and recovering 1,3-dichlorobenzene from a starting mixture of 1,3- and 1,4-dichlorobenzenes.

Another object of the invention is to provide a process including the step of selectively alkylating a mixture of 1,3- and 1,4-dichlorobenzenes to yield dichloroalkylbenzenes without production of undesirable by-products.

Still other objects and advantages of the invention will in part be obvious and will in part be apparent from the specification.

BRIEF DESCRIPTION OF THE DRAWINGS

FIG. 1 is a diagram showing the steps in the process of the invention.

DETAILED DESCRIPTION OF THE PREFERRED EMBODIMENTS

The process of the invention includes selective alkylation of an isomeric mixture of dichlorobenzenes to yield a mixture having 2,4-dichloroalkylbenzene as one of the components; isomerization of the 2,4-dichloroalkylbenzene in the presence of aluminum chloride as catalyst to yield an isomeric mixture of dichloroalkylbenzenes; separation of the 1,4-dichlorobenzene and unreacted 1,3-dichlorobenzene from the isomeric dichloroalkylbenzenes; and selective transalkylation of the dichloroalkylbenzenes to yield alkylbenzene, 3,5-dichloroalkylbenzene and 1,3-dichlorobenzene. Production of undesirable by-products is minimized by limiting conversion to less than about 50% of the 1,3-dichlorobenzene in the selective alkylation step.

The process proceeds according to the following reaction scheme:

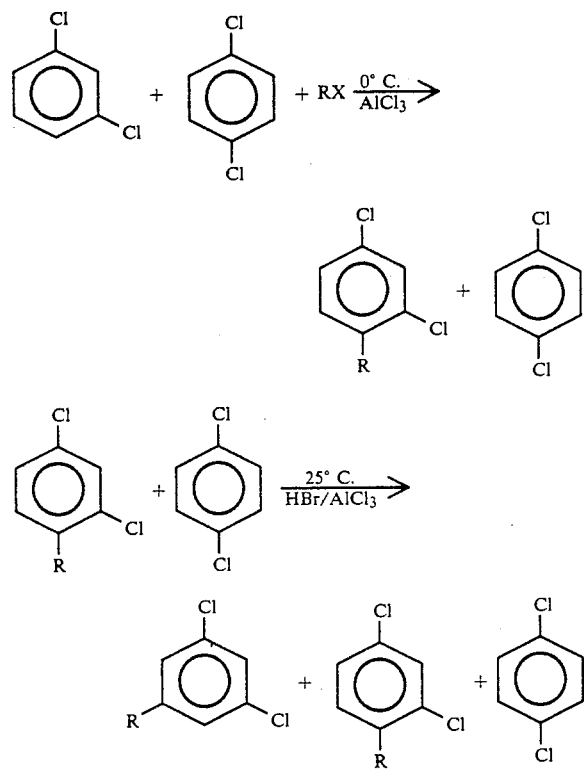

The product of second reaction is then subject to distillation wherein the 1,4-dichlorobenzene is readily separated from the alkylated benzenes. These latter compounds are then reacted in the final step of the process as depicted below:

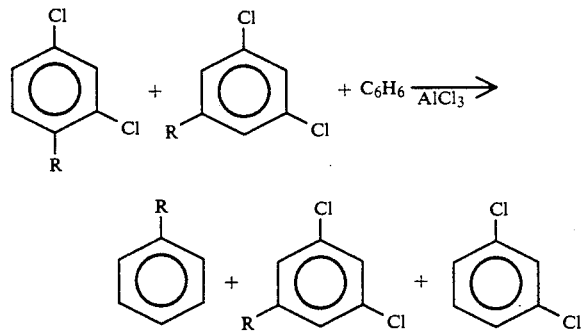

(1) Selective Alkylation

The selective alkylation of 1,3-dichlorobenzene in the isomeric mixture of 1,3- and 1,4-dichlorobenzene is achieved by preferentially reacting 1,3-dichlorobenzene with a suitable alkylating agent.

Alkylating agents suitable for use in the selective alkylation step include olefins, alkylhalides and aliphatic alcohols having 1 to 9 carbon atoms. Exemplary alkylating agents are propylene, isopropyl bromide, isopropyl chloride, isopropanol, n-propyl bromide and s-butyl chloride.

A catalytic amount of $AlCl_3$ is used to catalyze the selective alkylation. In a preferred embodiment, the catalytic amount is between about 0.1% and 20% by weight based on the weight of the 1,3-dichlorobenzene, more preferably, between about 0.1% and 2.0%. To achieve the advantages of the invention, less than 50% of the 1,3-dichlorobenzene should be converted to the 2,4-dichloroalkylbenzene, preferably, between 40% and 48%. Most preferably, only about 45% should be converted. Waste fractions are reduced since lower levels of dialkylated products are generated in the alkylation step when the conversion is so limited. Furthermore, by using this procedure essentially all of the alkylating agent is reacted.

The temperature range of the selective alkylation reaction is maintained between about $-10°$ C. and $10°$ C., preferably between about $0°$ and $4°$ C. This is accomplished by controlled addition of the alkylating agent during the course of the reaction. Maintenance of this temperature range is important since higher temperatures lead to increased levels of by-products. When isopropyl bromide is used as the alkylating agent, hydrogen bromide is generated in stoichiometric amounts. When propylene is used as the alkylating agents, hydrogen chloride or hydrogen bromide are not normally released. The selective alkylation product is a mixture of 2,4-dichloroalkylbenzene, 3,5-dichloroalkylbenzene, 1,4-dichlorobenzene and unreacted 1,3-dichlorobenzene. When propylene or isopropyl halide is used as the alkylating agent, 2,4-dichlorocumene with a small amount of 3,5-dichlorocumene are produced.

(2) Isomerization

In the second step of the process, the 2,4-dichloroalkylbenzene, preferably 2,4-dichlorocumene, is isomerized to the 3,5-isomer in the presence of an isomerization catalyst.

The catalyst used for the isomerization step is selected from the class of $AlCl_3.HCl$, $AlCl_3.HBr$, $AlCl_2Br.HBr$, $AlClBr_2.HBr$ and $AlBr_3.HBr$. Preferred catalysts are $AlCl_3.HCl$ and $AlCl_3.HBr$. The concentration of $AlCl_3$ may vary from 5% to 50%. The preferred level is 10 and 20% by weight of $AlCl_3$ based on the starting weight of the 1,3-dichlorobenzene. Aluminum chloride in amounts greater than about 20% does reduce the reaction time, but also produces additional unwanted compounds. During the isomerization step, HBr or HCl are used as an activating agent for the aluminum chloride catalyst.

The temperature for the isomerization step is maintained between about $10°$ and $60°$ C., preferably between about $20°$ and $30°$ C. This is accomplished by gradually raising the temperature to $25°$ C. following the selective alkylation step and constantly stirring the reaction mass. A reaction temperature above $30°$ C. generally leads to increased levels of dialkylated compounds and a corresponding reduction in yield to 3,5-dichlorocumene.

The degree of isomerization is dependent on reaction time. Under preferred conditions isomerization of up to 70% of the 2,4-isomer can be achieved within the first 2 hours at a temperature of about $25°$ C. After that, the reaction slows down. A reaction time of at least 5 hours is necessary to obtain 80% isomerization. Isomerization of 90% cannot be achieved even after 72 hours suggesting the existence of a thermodynamic equilibrium of approximately 85% 3,5-dichlorocumene and 15% 2,4-dichlorocumene.

(3) Separation

Following the isomerization, the 1,4-dichlorobenzene and unreacted 1,3-dichlorobenzene are separated, e.g., by distillation, from the reaction mixture. The 1,4-dichlorobenzene and 1,3-dichlorobenzene may be distilled under vacuum leaving behind an isomeric mixture of dichloroalkylbenzenes.

(4) Selective Transalkylation

The isomeric mixture of dichloroalkylbenzenes is selectively transalkylated in the presence of excess alkyl group receptor compound, e.g., benzene, and an aluminum chloride catalyst, to yield alkylbenzene, 3,5-dichloroalkylbenzene and 1,3-dichlorobenzene. An excess of the receptor compound is essential for complete transalkylation of the 2,4-dichloroalkylbenzene. A preferred receptor compound for this reaction is benzene. Generally, at least double the amount of benzene necessary on a per mole basis is used to ensure complete transalkylation of the 2,4-dichloroalkylbenzene. Other receptor compounds which can be used for the purpose of this invention include alkyl benzenes, such as toluene and xylenes, biphenyl, phenol, naphthalene, aniline, cresol, cyclohexanol and cyclohexanone.

When the alkyl group is an isopropyl group and the receptor compound is benzene, the alkylbenzene is cumene and the 3,5-dichloroalkylbenzene is 3,5-dichlorocumene. These compounds can be separated from each other by conventional separation techniques such as distillation. The 3,5-dichlorocumene produced by this process is more than 98% pure as are the 1,3-dichlorobenzene and the cumene.

The transalkylation step may be carried out at a temperature of from 20° to 80° C., preferably from 40° to 60° C., and more preferably at about 60° C. for a period of between about 2 and 5 hours, preferably between about 2 and 3 hours.

An aluminum chloride catalyst is used for the reaction. In a preferred embodiment the aluminum chloride level is 0.1 to 1.0% based on dichloroalkylbenzenes.

FIG. 1 is a diagram showing an exemplary process of the invention. As shown, 3050 lbs. (20.7 mole) of an isomeric mixture of dichlorobenzenes is introduced to the alkylation step. The isomeric mixture includes 70% meta-dichlorobenzene (2135 lb.; 14.5 mole) and 30% para-dichlorobenzene (915 lb.; 6.2 mole). An AlCl₃ catalyst (320 lb.; 2.40 mole) and isopropyl bromide (893.2 lb.; 7.3 mole) are added. The reaction generates HBr which is fed to a caustic scrubber. The alkylation reaction mass is fed directly to the isomerization step where isomerization takes place.

Any HCl/HBr gas that may be generated is fed to the scrubber. At the completion of the isomerization step, the reactor mass is sent to a wash step where it is washed with water followed by 10% caustic. The aqueous phase is sent to wastewater treatment and the organic phase is fed to a distillation step. In the distillation step an isomeric dichlorobenzene fraction totaling 1883.4 lbs. (12.8 mole) is recovered. The isomeric dichlorobenzene fraction consists of 53.84% meta-dichlorobenzene (1014.1 lb; 6.9 mole) and 46.16% para-dichlorobenzene (869.3 lbs; 5.9 mole). The main distillation fraction consisting of 85% 3,5-dichlorocumene and 15% 2,4-dichlorocumene and including 1304.3 lb. dichlorocumene (6.9 mole) is recovered and sent directly to a transalkylation step leaving behind a distillation residue consisting primarily of dialkylated dichlorobenzenes.

The transalkylation step is carried out using AlCl₃ (9.2 lbs.; 0.07 mole) and benzene (161.6 lbs.; 2.1 mole). Any HCl gas that may be generated is fed to a scrubber. At the completion of the transalkylation step, the reaction mass is washed with water followed by 10% caustic. The aqueous phase is sent to wastewater treatment and the organic phase is subjected to a distillation step which yields 73.0 lb. benzene (0.9 mole), 112.3 lb. cumene (0.9 mole), 137.3 lb. meta-dichlorobenzene (0.9 mole) and 1,000 lb. 3,5-dichlorocumene (5.3 mole). The distillation generates a heavy ends stream which is purged and disposed of.

The process will be better understood with reference to the following examples. These examples are presented for purposes of illustration only and are not to be construed as limiting.

EXAMPLE 1

This example shows that by limiting the conversion of 3,5-dichlorobenzene to below 50%, the dialkyl formation can be reduced and therefore the yield of 3,5-dichlorocumene can be improved. The conversion is limited by using only 0.45 moles of the alkylating agent for each mole of the m-dichlorobenzene.

377.8 (2.57 mole) of a mixture containing 70% (264.6 g; 1.8 mole) m-dichlorobenzene and 30% (113.2 g; 0.77 mole) p-dichlorobenzene and 48.0 g (0.36 mole) AlCl₃ are placed in a 4-neck one-liter jacketed flask equipped with thermometer, condenser, laboratory stirrer and graduated additional funnel. The coolant at −10° C. is passed through the jacket of the reaction flask and through the condenser. The outlet of the condenser is connected through an empty reservoir to a scrubber containing 10% caustic solution to absorb liberated HBr gas. The contents of the reaction flask are stirred with electric stirrer and 99.63 g (0.81 mole) isopropyl bromide is added to the reaction flask from a graduated additional funnel dropwise below the liquid level over a period of one hour. The temperature of the reaction mixture is maintained at −5° to 5° C. during the addition. The reaction mixture is stirred for an additional one-half hour at this temperature to complete the alkylation and then coolant removed from the jacket and the condenser to let the temperature of the reaction mixture rise to room temperature. When the reaction mixture reaches room temperature, the condenser outlet leading to dilute caustic solution is replaced by a CaCl₂ drying tube and the reaction mixture is allowed to stand at room temperature overnight. At this point, chromatographic analysis of the isomerization product shows 85% 3,5- and 15% 2,4-dichlorocumene isomers.

The reaction mixture is cooled again to −10° C. by passing coolant in the jacket of the reaction flask, 150 ml of water is added very slowly so that the temperature does not exceed 20° C. to decompose the catalyst complex. The organic layer is separated, washed twice with 150 ml water (each time) and dried over anhydrous Na₂SO₄. A 398 g dried organic layer is obtained.

The organic layer is fractionally distilled using a fractionating column under 15–20 mm vacuum. First 1,4-dichlorobenzene and unreacted 1,3-dichlorobenzene are removed; and then a fraction (130 g; 0.688 moles) of isomers consisting of 20% (26.0 g; 0.138 moles) 2,4- and 80% (104.0 g; 0.55 moles) 3,5-dichlorocumene is isolated. This demonstrates that 3,5-dichlorocumene can be obtained in high yield from 1,3- and 1,4-dichlorobenzene.

EXAMPLE 2

This example describes the procedure used to separate 3,5-dichlorocumene from a mixture of 3,5- and 2,4-dichlorocumenes by transalkylation. The 130 g fraction from Example 1 is added to a 500 ml, 4-neck flask equipped with a water condenser, electric stirrer, thermometer and additional funnel. While stirring, 2.16 g (0.016 mole) aluminum chloride is first added to the reaction mixture. Thereafter, through an additional funnel, 83.5 g (1.07 mole) benzene is added in one shot. The reaction mixture is then heated to 60° C. and kept at this temperature for two hours. The reaction mixture is cooled to 0° C. with an ice bath and then 10 ml of water are added to decompose the aluminum chloride catalyst. The organic layer is separated, washed with water two times, dried over anhydrous $NA_2SO_4$ and fractionally distilled using a fractionating column under 15–20 mm pressure. First benzene, cumene and m-dichlorobenzene fractions are removed and then 87 g (80% of expected yield) of 98% pure 3,5-dichlorocumene is isolated.

COMPARATIVE EXAMPLE 1

This example shows that over 99% conversion of 1,3-dichlorobenzene can be achieved by using a mole/mole ratio of the alkylating agent, but the yield will be reduced.

This experiment is carried out in the same manner as in Example 1, except a mole to mole ratio of alkylating agent to m-DCB, is used. Thus, 377.8 g (2.57 mole) of a mixture consisting of 70% (264.6 g; 1.8 mole) m-dichlorobenzene and 30% (113.2 g; 0.77 mole) p-dichlorobenzene and 48.0 g (0.36 mole) $AlCl_3$ are placed in a 4-neck, one-liter flask and 221.4 g (1.8 mole) isopropyl bromide is added to the reaction mixture over a period of 2 hours.

After overnight isomerization, decomposition of the complex with water and fractional distillation, 238 g (70% of theory) an isomeric mixture, consisting of 75% 3,5-dichlorocumene is obtained. This is considerably less than the 85% of theory obtained in Example 1.

EXAMPLE 3

This experiment is carried out in the same manner as in Example 1, except isopropyl chloride instead of isopropyl bromide is used as an alkylating agent. Thus, 377.8 g (2.57 mole) of mixture consisting of 70% (264.6 g; 1.8 mole) m-dichlorobenzene, 30% (113.2 g; 0.77 mole) p-dichlorobenzene and 48.0 g (0.36 mole) $AlCl_3$ are placed in a 4-neck, one-liter flask and to it 65.58 g (0.81 mole) isopropyl chloride is added. After overnight stirring, decomposition of the complex with water and fractional distillation, 107 g (70% of theory) of dichlorocumene consisting almost entirely of 2,4-dichlorocumene isomer is obtained. This example shows that the alkylation proceeds with isopropyl chloride, but that no isomerization took place under the reactions condition of Example 1.

COMPARATIVE EXAMPLE 2

This experiment is carried out in the same manner as in Example 1, except that propylene is used instead of isopropyl bromide. A dry-ice condenser is used instead of coolant condenser and propylene is sparged below the liquid level through a sparger tube. Thus, 377.8 g (2.57 mole) of mixture consisting of 70% (264.6 g; 1.8 mole) m-dichlorobenzene, 30% (113.2 g; 0.77 mole) p-dichlorobenzene and 48.0 g (0.36 mole) $AlCl_3$ are placed in a 4-neck, one-liter flask and to it 34 g (0.81 mole) propylene is sparged below the liquid level. The temperature of reaction mixture is kept below 10° C. After overnight isomerization, decomposition of the $AlCl_3$ complex, the organic layer shows little alkylation: only 1 to 2% dichlorocumene is formed.

EXAMPLE 4

This experiment is carried out in the same manner as Comparative Example 2, except that an $AlCl_3.HBr$ complex is first formed and then propylene added. Specifically, 377.66 g (2.297 mole) of mixture consisting of 70% (236.23 g; 1.607 mole) m-dichlorobenzene, 30% (101.43 g; 0.69 mole) p-dichlorobenzene and 42.85 g (0.3214 mole) $AlCl_3$ are placed in a 4-neck, one-liter flask and to it 26 g (0.32 mole) HBr are sparged below the liquid level. Then 30.37 g (0.72 mole) propylene is sparged below the liquid level, keeping the temperature of reaction mixture below 10° C. After standing overnight, $AlCl_3$ complex decomposition, water washings and drying, a 351.6 g organic layer is obtained. This organic layer is fractionally distilled, isolating 98.5 g (72% theory) of an isomeric mixture containing approximately 80% 3,5-dichlorocumene. This clearly shows that the presence of $AlCl_3.HBr$ complex is required for the isomerization when propylene is used as the alkylating agent.

EXAMPLE 5

This example shows that $AlCl_3.HCl$ can also be used as the catalyst with a propylene alkylation agent.

This experiment is carried out in the same manner as in Example 4, except instead of HBr, 11.75 g (0.32 mole) HCl is sparged below the liquid level. The isomerization is carried at room temperature for 60 hours and the reaction mixture then heated to 40° C. for four hours. The reaction is then quenched and the organic layer separated and fractionally distilled, isolating an isomeric mixture containing approximately 50% 3,5-dichlorocumene. This shows that under given reaction conditions, the HBr complex is more active than the HCl complex.

EXAMPLE 6

This example shows that the HBr needed for the activation of $AlCl_3$ can be generated in the initial stages of the reaction by using isopropyl bromide (until enough HBr is produced to form $AlCl_3.HBr$) with propylene as the primary alkylating agent.

A one liter jacketed reaction flask equipped with a lab stirrer, a condenser, a thermometer, and an addition funnel is used. The reactor is cooled to −5° C. by coolant from a circulating bath. A mixture containing 70% 1,3- and 30% 1,4-dichlorobenzene is charged to the reactor such that 664.4 grams of 1,3-dichlorobenzene (4.52 moles) is present. 133 grams (1.0 mole) anhydrous aluminum chloride is transferred to the reactor while the reaction mass is stirred. 139 grams of isopropyl bromide (1.13 moles) is then added to the reactor over a period of 2 hours. The reaction temperature is kept at about 0° C. during the addition. The condenser is cooled to −35° C. to avoid the escape of the HBr generated during the reaction. At the end of isopropyl bromide addition, propylene is introduced into the reaction mixture through a fine sparger located under the liquid surface. The addition of propylene is controlled to keep the reaction temperature between 0° and 4° C. A total of 64.70 grams (1.54 moles) of propylene is added to the reactor during a two hour period. At the conclusion of the propylene addition, the reactor temperature is gradually increased to 20° C. and left overnight to complete the isomerization. The reaction product is quenched by the careful addition of water and the organic layer then separated and dried over anhydrous sodium sulfate. The organic layer is then fractionally distilled to isolate 423.8 grams (83.9% theory) of an isomeric mixture containing 78.9% 3,5-dichlorocumene.

The above process is particularly preferred because outstanding results are achieved and the amount of costly isopropyl bromide is minimized.

EXAMPLE 7

This example shows that alkylation and transalkylation can be achieved in a single reactor without intermediate purification of the dichlorocumene fractions.

In this experiment, the selective transalkylation of 2,4-dichlorocumene is carried out without the work-up or distillation of the alkylation/isomerization reaction product. In contrast, Example 2 shows the transalkylation of the pure mixture of 2,4- and 3,5-dichlorocumenes. The alkylation/isomerization reaction is carried out as described in Example 1. The chromatographic analysis of the product after isomerization indicates the presence of an isomeric mixture containing approximately 80% 3,5-dichlorocumene. Transalkylation is initiated by adding 95 g (1.22 mole) benzene to the reaction mixture with stirring at room temperature for two hours. Analysis of the sample at this stage shows only 3,5-dichlorocumene and no peak for 2,4-dichlorocumene indicating that the transalkylation is completed. The reaction mixture is cooled to −10° C. by passing coolant through the outer jacket of the reaction flask. Water (150 ml) is added very slowly to keep the temperature at less than 20° C. The organic layer is separated, washed twice with 150 ml water, dried over anhydrous Na$_2$SO$_4$ and weighed. A dry organic layer (450 g) is obtained.

The organic layer is fractionally distilled using a fractionating column under 15-20 mm vacuum. First benzene, cumene, 1,3- and 1,4-dichlorobenzene are removed and then 55 g (0.29 mole) of pure 3,5-dichlorocumene is isolated. This represents a 42% yield based on the alkylating agent. This process is particularly useful when it is desired to obtain only 3,5-dichlorocumene without the formation of 1,3-dichlorobenzene as a coproduct.

What is claimed is:

1. A process for recovering 1,3-dichlorobenzene and synthesizing 3,5-dichlorocumene comprising:
   selectively alkylating the 1,3-dichlorobenzene in a mixture of 1,3-dichlorobenzene and 1,4-dichlorobenzene with a propylene or isopropyl halide alkylating agent in the presence of a catalytic amount of an aluminum halide at a temperature of from −10° to +20° C. to form a product containing 2,4-dichlorocumene;
   isomerizing the 2,4-dichlorocumene in said product to 3,5-dichlorocumene in the presence of an activated aluminum halide catalyst at a temperature of from 10° to 60° C. to yield an effluent of 1,4-dichlorobenzene, 2,4-dichlorocumene, and 3,5-dichlorocumene;
   separating the 1,4-dichlorobenzene and a mixture of 2,4- and 3,5-dichlorocumene from said effluent; and
   selectively transalkylating the 2,4- and 3,5-dichlorocumene in the presence of an alkyl group receptor and an aluminum halide catalyst at a temperature of from 20° to 80° C. to yield 3,5-dichlorocumene and 1,3-dichlorobenzene.

2. The process of claim 1 wherein less than 50% of the 1,3-dichlorobenzene in the first mixture is selectively alkylated to 2,4-dichloroalkylbenzene.

3. The process of claim 1 wherein the alkylating agent is an isopropyl halide.

4. The process of claim 1 wherein the alkylating agent is isopropyl bromide.

5. The process of claim 1 wherein the alkylating agent is isopropyl chloride.

6. The process of claim 2 wherein the alkylating agent is propylene.

7. The process of claim 1 wherein the propylene and isopropyl bromide serve as the alkylating agent.

8. The process of claim 1 wherein the reaction mixture from the alkylation step is isomerized directly to produce 3,5-dialkylcumene.

9. The process of claim 1 wherein the receptor is benzene.

10. The process of claim 1 wherein the isomeric mixture is selectively transalkylated in the presence of excess benzene.

11. The process of claim 1 wherein from 0.4 to 0.5 mole of the alkylating agent is present for each mole of 1,3-dichlorobenzene.

12. The process of claim 1 wherein the aluminum halide has been activated by anhydrous hydrogen bromide.

13. The process of claim 12 wherein the aluminum halide catalyst is aluminum chloride.

14. The process of claim 1 wherein the alkylation reaction is carried out at a temperature of from −5° to +10° C.

15. The process of claim 1 wherein the isomerization is carried out at from 20° to 50° C.

16. The process of claim 1 wherein from 0.1 to 1% by weight of the aluminum halide, based on weight of dichlorocumene, is used as the catalyst in the transalkylation step.

17. The process of claim 1 wherein the transalkylation is carried out at a temperature of from 30° to 70° C.

18. The process of claim 1 wherein the transalkylation is completed in from 2 to 5 hours.

19. A process for recovering 1,3-dichlorobenzene and synthesizing 3,5-dichlorocumene comprising:
   selectively alkylating less than 50% of the 1,3-dichlorobenzene in a mixture of 1,3-dichlorobenzene and 1,4-dichlorobenzene with a propylene or isopropyl halide alkylating agent at a temperature of from −5° to +10° C. to form a product containing 2,4-dichlorocumene; and
   isomerizing the 2,4-dichlorocumene in said product to 3,5-dichlorocumene in the presence of an aluminum halide catalyst activated with anhydrous hydrogen bromide at a temperature of from 25° to 35° C. to yield an effluent of 1,4-dichlorobenzene, 2,4-dichlorocumene, and 3,5-dichlorocumene.

20. The process of claim 19, wherein the mixture of 1,4- and 1,3-dichlorobenzenes is selectively alkylated using an alkyl halide alkylating agent having between about 1 and 9 carbon atoms in the alkyl group.

21. The process of claim 19, wherein the alkylating agent is isopropyl bromide.

22. The process of claim 19 wherein the alkylating agent is propylene.

* * * * *